US006916302B2

(12) United States Patent
Gehrke

(10) Patent No.: US 6,916,302 B2
(45) Date of Patent: Jul. 12, 2005

(54) APPENDAGE ELEVATOR SYSTEM

(76) Inventor: Jon C. Gehrke, 1837 NW. 152nd Ct., Clive, IA (US) 50325

(*) Notice: Subject to any disclaimer, the term of this patent is extended or adjusted under 35 U.S.C. 154(b) by 205 days.

(21) Appl. No.: 10/038,240

(22) Filed: Oct. 19, 2001

(65) Prior Publication Data

US 2003/0078527 A1 Apr. 24, 2003

(51) Int. Cl.$^7$ .................................................. A61F 5/00
(52) U.S. Cl. ........................ 602/36; 248/125.1; 248/127
(58) Field of Search .................... 248/122.1, 125.3, 248/124.1, 125.1, 125.2, 125.8, 125.9, 130, 131, 157, 423, 424, 425, 311.3, 127, 161, 407, 408; 602/32–40, 20, 62, 21; 403/377; 51/659, 505.1, 660

(56) References Cited

U.S. PATENT DOCUMENTS

| 589,806 | A | * | 9/1897 | Bard ............................. 251/7 |
| 1,021,688 | A | * | 3/1912 | Le Jeune ...................... 602/33 |
| 1,301,565 | A | * | 4/1919 | Jacobs ......................... 285/319 |
| 2,642,589 | A | * | 6/1953 | Cobb ........................... 5/505.1 |
| 2,658,506 | A | * | 11/1953 | Haskell ........................ 602/32 |
| 2,710,414 | A | | 6/1955 | Emery |
| 3,026,079 | A | * | 3/1962 | Stack ........................ 248/122.1 |
| 3,068,859 | A | * | 12/1962 | Treutelaar .................... 602/32 |
| 3,274,998 | A | * | 9/1966 | Grier, Jr. ...................... 602/23 |
| 3,298,364 | A | * | 1/1967 | Radford ........................ 602/33 |
| 3,298,648 | A | | 1/1967 | Sepanski |
| 3,390,675 | A | * | 7/1968 | Giannestras .................. 602/33 |
| 3,662,750 | A | * | 5/1972 | Jorgensen ..................... 602/32 |
| 3,693,617 | A | * | 9/1972 | Trott ............................ 602/40 |
| 3,804,355 | A | * | 4/1974 | Uroshevich .............. 248/124.1 |
| 4,145,006 | A | * | 3/1979 | Webb ............................ 269/69 |
| 4,209,080 | A | * | 6/1980 | Douglas .................... 184/6.16 |
| 4,232,664 | A | * | 11/1980 | Blatt ............................. 602/4 |
| 4,445,506 | A | * | 5/1984 | Johansson et al. ............. 602/39 |
| 4,493,121 | A | | 1/1985 | Williams |
| 4,541,596 | A | * | 9/1985 | Price ......................... 248/125.8 |
| 4,570,275 | A | | 2/1986 | Merriman |
| 4,616,637 | A | * | 10/1986 | Caspari et al. ................ 602/39 |
| 4,725,027 | A | * | 2/1988 | Bekanich ................. 248/125.8 |
| 4,730,610 | A | * | 3/1988 | Graebe ........................ 128/882 |
| 4,841,589 | A | | 6/1989 | Moore |
| D306,667 | S | | 3/1990 | Fedder |
| 5,181,681 | A | * | 1/1993 | Edwards .................. 248/125.1 |
| 5,320,348 | A | * | 6/1994 | Starrett ...................... 463/47.6 |
| 5,435,028 | A | | 7/1995 | Frala |
| 5,470,037 | A | * | 11/1995 | Willis ....................... 248/125.9 |
| 5,735,806 | A | * | 4/1998 | Leibovic ...................... 602/32 |
| 5,785,057 | A | | 7/1998 | Fischer |
| 5,868,694 | A | * | 2/1999 | Marlow et al. ............... 602/32 |
| 5,957,135 | A | * | 9/1999 | Molina ........................ 128/845 |
| 6,083,182 | A | * | 7/2000 | Fries ............................. 602/4 |
| 6,095,714 | A | * | 8/2000 | Spencer ...................... 403/377 |
| 6,238,361 | B1 | * | 5/2001 | Poirier ........................ 602/33 |
| 6,302,614 | B1 | * | 10/2001 | Tseng ...................... 403/109.5 |

* cited by examiner

Primary Examiner—Gregory L. Huson
Assistant Examiner—Huong Q. Pham
(74) Attorney, Agent, or Firm—Brian J. Laurenzo; Jason M. Hunt; Angela E. Dralle

(57) ABSTRACT

A device for support and elevation of a limb. More specifically, the invention is a system for elevating a limb, comprising an adjustable sling assembly that can be attached by a hook to a support member that provides the elevation, which in turn can be inserted into either a freestanding base or a base designed for placement between a mattress and box spring. Thus, the elevator system can be used effectively when a person is in both a sitting and a supine position. The elevator system is vertically adjustable by varying the distance between the hook and the sling or by adjusting the telescoping support sections of the support assembly. The elevator system is lightweight, easily disinfected, and can be disassembled or collapsed for ease in transport and storage. The elevator system is also relatively inexpensive to manufacture and is intended both for hospital and home use.

10 Claims, 10 Drawing Sheets

APPENDAGE ELEVATOR SYSTEM

BACKGROUND OF THE INVENTION

The present invention relates to devices used in supporting and elevating limbs. More specifically, the invention is an elevation system with a sling support mechanism that can be attached to one of two interchangeable base portions for use by a patient recovering from medical procedures or medical conditions while the patient is positioned in either a sitting or supine position.

There is a need for a product that effectively suspends a limb in a variety of different positions. After orthopedic or other types of surgery or procedures such as a mastectomy, there is often a need for a limb, often an arm, to be elevated to aid in healing. Elevation is beneficial to recovery because it reduces or eliminates swelling and fluid build-up (edema). Also, patients suffering from chronic lymphoedema may require limb elevation therapy on a permanent basis.

Elevation is normally provided in the hospital after surgery and is often recommended to patients after they leave the hospital. However, the devices currently in use do not provide an effective elevator system for use both at home and at the hospital. Generally, to elevate a limb, a sling is attached to a support that is positioned higher than the patient, and the limb is inserted into the sling. For optimal effect, after some procedures, an arm should be supported in a bent configuration with the upper arm in a horizontal position and the lower arm, or forearm, in a vertical position with the elbow in a position that is lower than the hand. Although some health care workers may improvise and attempt to hang a sling from a stand designed for another purpose, such as a stand used to administer intravenous fluid, such attempts may be unsuccessful due to the angle or height of the stand used. In addition, the use of other hospital stands do not fully accommodate patients' needs because the stands are not designed for, nor are they feasible for home use, due to weight, bulk, or expense, and current stand mechanisms generally are not designed such that any one device can be used by a patient for elevation in multiple body positions, such as lying supine or sitting in a chair. At home, patients may try to support the limb using several pillows. Pillows are cumbersome, and often do not provide the correct positioning of the limb which is needed to achieve optimum elevation therapy. In addition, pillows can shift and compress, causing the patient annoyance and discomfort, especially during sleeping or resting periods.

Although there are a variety of stands used to suspend bedclothes away from a patient's body and to position medical devices such as intravenous fluid bags, most are not designed in such a way to be efficiently used for hanging a sling and elevating a limb. For example, some stands intended for other purposes are vertically adjustable to some degree, but often the vertical adjustment range is too limited, or requires the adjustment to be made in pre-determined increments. (See U.S. Pat. No. 3,026,079). Other stands are either too cumbersome, cannot be utilized without the mattress support, are lacking adjustment mechanisms, or provide adjustment mechanisms that are too complex for feasible home use. (See, e.g., U.S. Pat. No. 4,841,589). Finally, stands such as the device in U.S. Pat. No. 4,541,596 are composed of many parts, making the stand expensive to manufacture and difficult to assemble, which can be prohibitive for home use by patients.

The present invention, on the other hand, consists of few parts that are easy manufacture, to assemble and to operate. The limb elevation system of the present invention also allows for virtually infinite adjustment of the sling elevation. A patient is not limited to six or eight elevator positions, but can adjust the elevation very precisely according to the specific needs. Furthermore, adjustment of the sling elevation of the present invention is easy, requiring only the re-positioning of the "Velcro" straps along the sling assembly. Additionally, the elevation can be varied by adjusting the telescoping support sections of the support assembly. The present invention also allows for the use of the support assembly interchangeably with two different bases to accommodate a sitting or supine position of the body. Thus, using the present invention, one system can accommodate elevation in multiple body positions.

The concept of using a sling supported by a device positioned above the body is suggested in U.S. Pat. No. 4,232,664, which teaches an L-shaped sling. The '664 indicates that the sling could be supported by a floor stand or bracket in the "usual fashion." Such "usual" floor stands or bed brackets known in the art are not designed to support a sling and are not designed in a way to ensure the proper positioning and elevation of a limb in a sling. Furthermore, to accomplish elevation in both the sitting and supine positions using other types of stands, two separate devices would be required. The present invention alleviates the need to purchase, transport and store multiple devices. Instead, with a minor adjustment, elevation can be provided in multiple settings with one system.

The present invention provides superior elevation by using a system of interchangeable pieces to support a limb in an elevated position. The present invention provides the patient with several options. The freestanding base and support may be used to suspend the limb while the patient is either sitting in a chair or lying down. However, when the patient desires elevation while lying supine in bed, a second base, which is designed to be positioned between a mattress and box spring, can be easily substituted for the freestanding base. There are a minimal number of pieces to purchase and to transport or adjust. Furthermore, the system is easy to assemble and disassemble. The preferred embodiment is constructed of lightweight, plastic pipe and connectors such as polyvinyl chloride (PVC) pipe. This material is inexpensive, so that it is feasible for patients to purchase the device and use it in the home. The PVC pipe also allows for easy disinfection of the system by wiping the elevation system with a surfactant or alcohol. This is a useful feature if the patient suffers from post-surgical drainage or for multiple users, in general, such as in a hospital. The present invention combines all of these useful features into one elevation system that is inexpensive, lightweight, portable and easy to use.

BRIEF SUMMARY OF THE INVENTION

The present invention provides an elevation system utilizing a sling supported by a pole attached to either a freestanding base or to a horizontal base supported by positioning the base between two flat surfaces such as a mattress and box spring. More specifically, the invention provides a system for limb elevation that is made of lightweight, easily disinfected material, in a design that is vertically adjustable, can be used in a variety of settings, and is collapsible for easy transport and storage.

The embodiment of the present invention results in advantages not provided by medical equipment stands designed for other purposes. The principal advantages of the present invention are that it provides a system, with two interchangeable bases, upon which to hang a sling, and the elevation of the sling can be easily adjusted to a wide variety of positions. The present invention is preferably constructed of lightweight, hollow material such as plastic pipe which makes transporting and disinfecting the equipment easier, while reducing the manufacturing costs so that, in combination with its other advantages, the system is feasible for home use.

It is one object of the present invention to provide a limb elevation system that is vertically adjustable and provides elevation in a variety of positions.

It is an additional object of the invention to provide a limb elevation system that is lightweight, yet sturdy, and is collapsible for storage and transfer.

Other objects, features, and advantages of the present invention will be readily appreciated from the following description. The description makes reference to the accompanying drawings, which are provided for illustration of the preferred embodiment and alternative embodiments. However, the drawings do not represent the full scope of the invention. The subject matter regarded as the present invention is particularly pointed out and distinctly claimed at the conclusion of this specification.

DETAILED DESCRIPTION OF THE INVENTION

Figure 1:
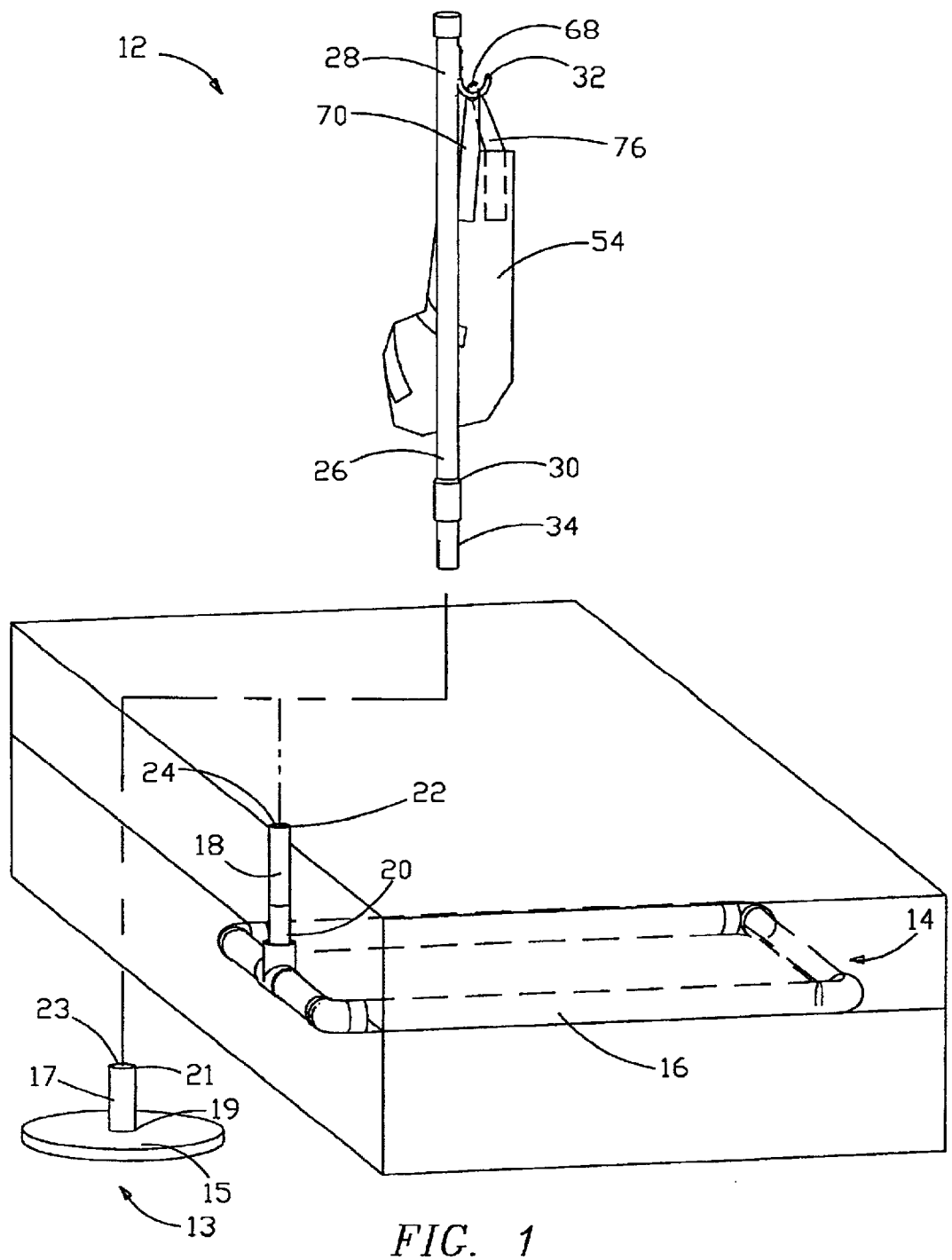
FIG. 1 is a perspective view of the appendage elevator system which represents the preferred embodiment of the present invention.

FIG. 1 represents the preferred embodiment of the appendage elevator system 12. In general, the invention is an appendage elevator system 12 comprised of a first base 13 and a second base 14, a support assembly 26, a hook 32, a connecter 34, a sling assembly 54, and a means for removably attaching the sling assembly 54 to the hook 32, such as the ring 68 and two straps 70, 76 as shown in FIG. 1. More specifically, the invention is an appendage elevator system 12 that can be adjusted by placing the two straps 70, 76 in varying positions on the sling assembly 54. The sling assembly 54 can then be attached by the hook 32 to a support assembly 26 that provides the elevation, which in turn can be inserted into either a first base 13 that is adapted to be free-standing when placed on a flat surface or into a second base 14 adapted to be supported between two opposing surfaces, such as between a mattress and box spring or between the cushions of a chair or sofa.

Figure 2:
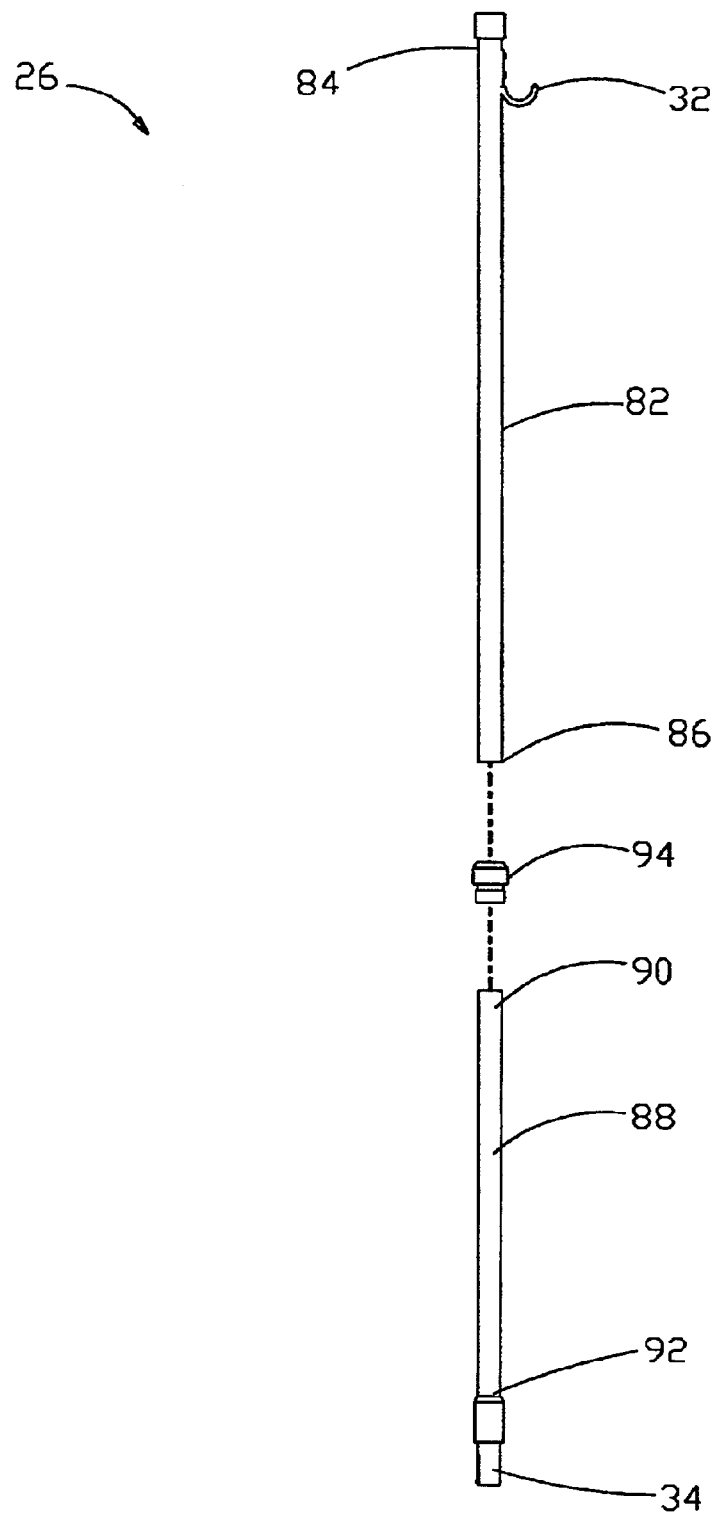
FIG. 2 is an exploded view of an alternative embodiment of the support assembly.

FIG. 1 shows the first base 13 having a weighted portion 15 that is adapted to rest upon the floor or another flat surface. The first base 13 has a first base attachment member 17 that is attached to and extends from the weighted portion 15 of the first base 13 such that the first base attachment member 17 is supported by the weighted portion 15. The first base attachment member 17 has a first end 19 and a second end 21. The first end 19 of the first base attachment member 17 is connected to the weighted portion 15 of the first base 13. The second end 21 of the first base attachment member 17 defines a hollow space 23 that is adapted to receive the second end 38 of the connecter 34 when the connector 34 is attached to the second end 30 of the support assembly 26 as shown in FIG. 2.

FIG. 1 also shows the second base 14 which is comprised of a horizontal frame 16 of a generally planar shape and a second base attachment member 18. The second base attachment member 18 has a first end 20 and a second end 22. The first end 20 of the second base attachment member 18 is attached to the horizontal frame 16 such that the second base attachment member 18 extends from and is supported by the horizontal frame 16. The second end 22 of the second base attachment member 18 defines an opening 24 to receive the second end 38 of the connector 34 when the connector 34 is attached to the second end 30 of the support assembly 26. Thus, the dashed lines of FIG. 1 show that the support assembly 26 can be placed into either the first base 13 or the second base 14, interchangeably. FIG. 1 shows the preferred embodiment having a second base 14 that is a rectangular shape. However, the rectangular shape is not an essential part of the present invention, and the base can be formed in a variety of shapes without altering the material features of the invention.

To use the invention, the support assembly 26 is inserted into one of the two bases 2, 14. A hook 32, which is attached to the first end 28 of the support assembly 26, is then used to suspend the sling assembly 54 from the support assembly 26, and the support assembly 26 is used to provide elevation of the limb.

The support assembly 26 of the appendage elevator system 12 has a first end 28 and a second end 30 and in the preferred embodiment is comprised of a single supporting member, as shown in FIG. 1. Alternatively, the support assembly 26 can be comprised of two support sections 82, 88 as illustrated in FIG. 2. Referring now to FIG. 2, the support assembly 26 can be comprised of a first support section 82 having a first end 84 and a second end 86 and a second support section 88 with a first end 90 and a second end 92. The two support sections 82, 88 of the support assembly 26 are adapted to be connected telescopically by inserting the first end 90 of the second support section 88 into the second end 86 of the first support section 82.

Figure 6:
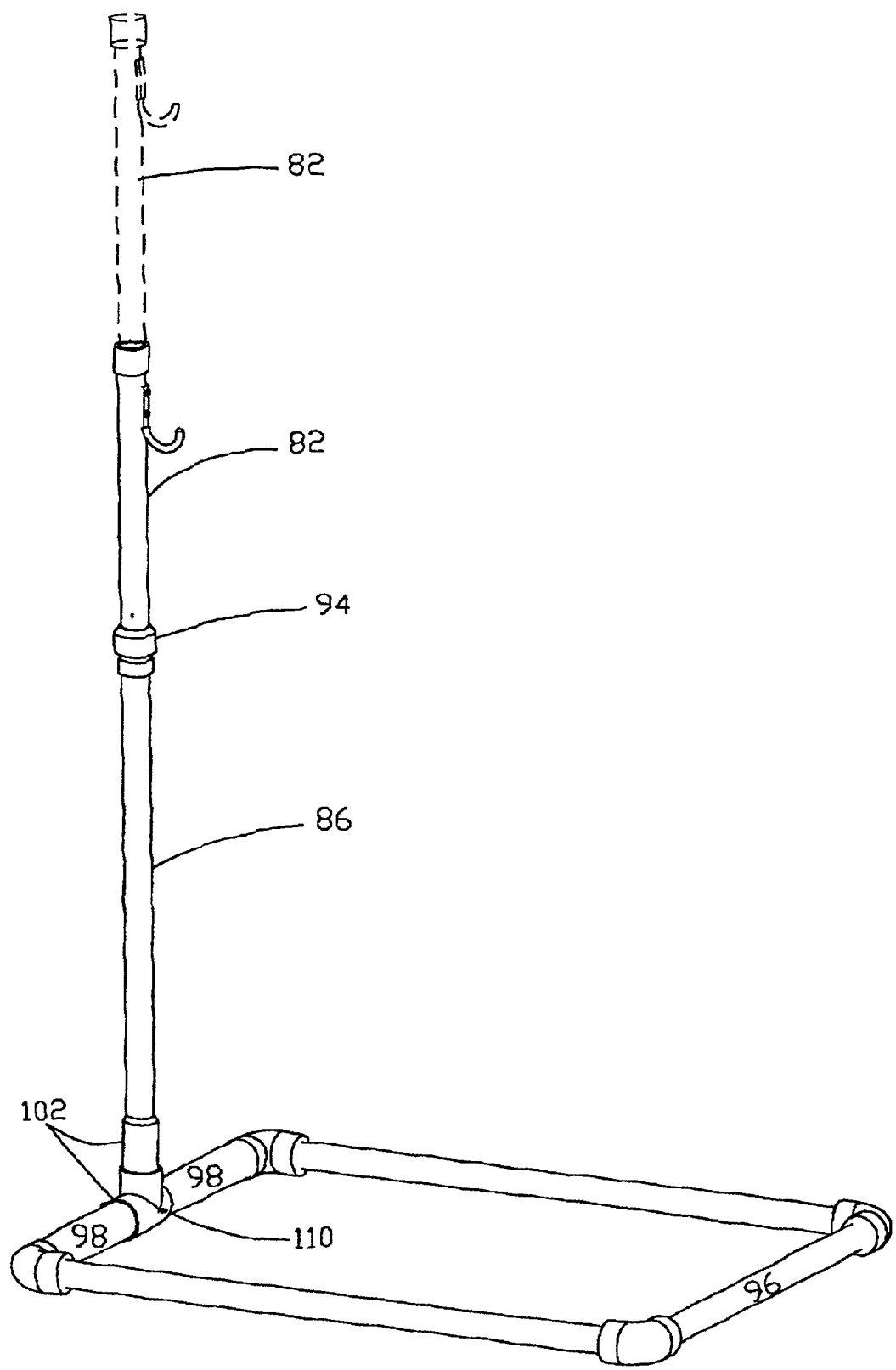
FIG. 6 is a perspective view of an alternative embodiment of the second base which utilizes a pin and aperture system.

While it is not necessary to make or use the invention, the first end 90 of the second support section 88 and the second end 86 of the first support section 82 can be threaded, allowing the user to change the telescopic position of the two support sections 82, 88 by twisting the two support sections 82, 88 relative to one another, thereby adjusting the height of the support assembly 26 and the elevation of the sling assembly 54. In the alternative embodiment of the support assembly 26 shown in FIG. 2, however, the two support sections 82, 88 are adapted such that the elevation of the support assembly 26 is altered by sliding the two support sections 82, 88 together in an overlapping telescopic fashion. A means, such as a clamping device 94, to selectively secure the first end 90 of the second support section 88 in a telescopic fashion relative to the second end 86 of the first support section 82 is also required. As shown in FIG. 2, the two support sections 82, 88 are secured by a means such as a clamping device 94 placed over the juncture of the two support sections 82, 88. However, a variety of means could be used to secure the two support sections 82, 88 in a desired position. The adjustment of the appendage elevator system 12 which utilizes the alternative embodiment of the support assembly 26 and is accomplished by changing the relative positions of the telescoping support sections 82, 88, is shown in FIG. 6 by the dashed phantom lines.

When the preferred embodiment, as shown in FIG. 1, is not in use, the support assembly 26 can be detached from either of the two bases 2, 14. Additionally, if the appendage elevation system 12 utilizes the alternative embodiment of the support assembly 26 as in FIG. 2, the two support sections 82, 88 can be disengaged by releasing the clamping device 94. The bases 2, 14 and the support assembly 26 can then be easily stored or transported, as each piece of the appendage elevator system 12 is relatively small and lightweight.

Figure 3:
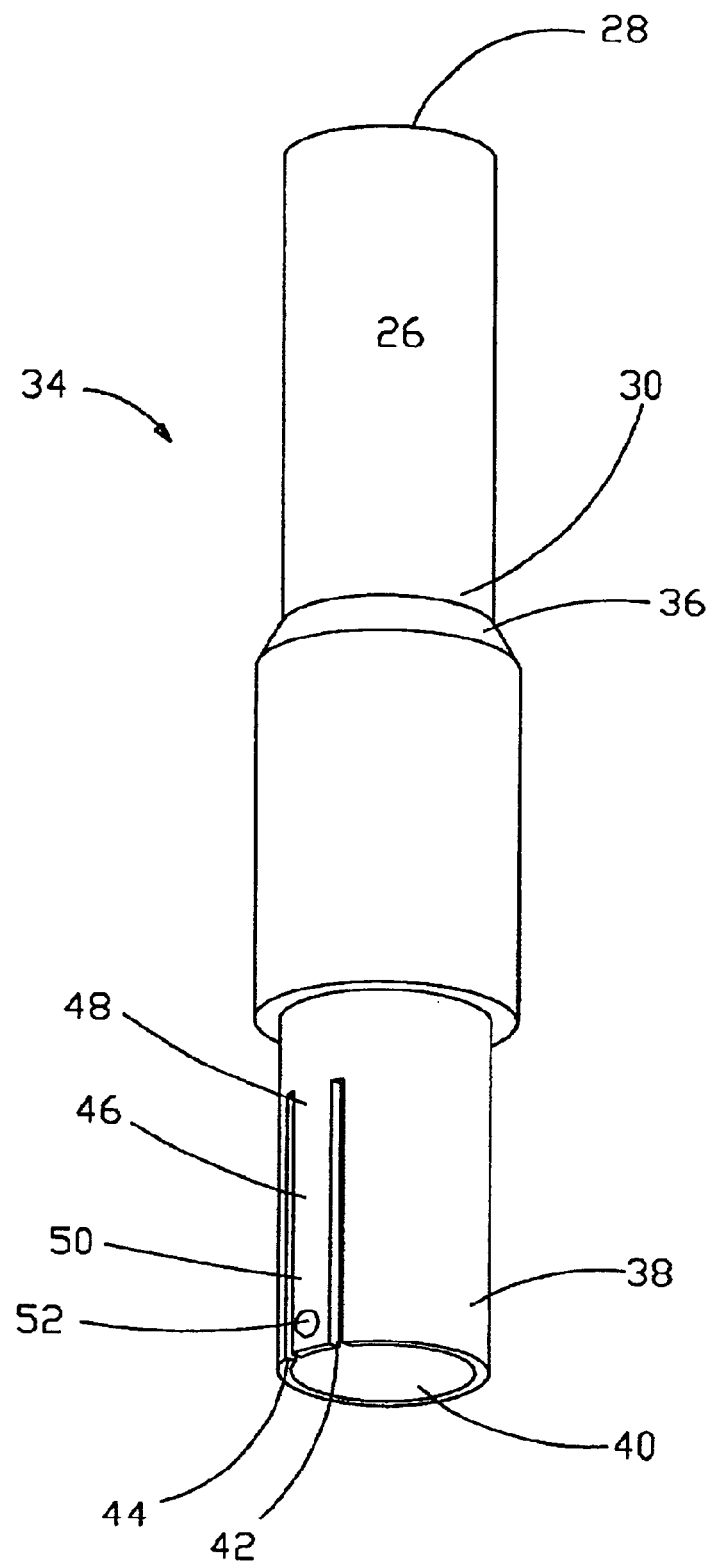
FIG. 3 is an enlarged, detailed view of the connector showing the tongue in a normal position.

Referring now to FIG. 3, the connector 34 that is used in the preferred embodiment to attach the support assembly 26 to either the first base 13 or the second base 14 is shown in detail. The connector 34 has a first end 36 which can be attached to the support assembly 26 and a second end 38 that is adapted to be inserted into the first base 13 or the second base 14, interchangeably. The connector 34 has a first groove 42 and a second groove 44 originating at the second end 38 of the connector 34 and extending into the connector 34 in a longitudinal fashion relative to the support assembly 26. The second groove 44 is substantially parallel to the first groove 42. The two grooves 42, 44 define a tongue 46 with a first end 48 and a second end 50. The first end 48 of the tongue 46 is attached to the second end 38 of the connector 34, and the second end 50 of the tongue 46 has a raised portion 52 that is adapted to frictionally engage an inside surface of the first base 13 or an inside surface of the second base 14 when the tongue 46 is released from a tensioned position and allowed to contact the inside surface of one of the bases 2, 14 when the connector 34 is inserted into one of the bases 2, 14. As shown in FIG. 3, the second end 38 of the connector 34 defines a hollow space 40. The second end 50 of the tongue 46 is movable between a normal position where the tongue 46 is substantially aligned with the second end 38 of the connector and a tensioned position where the tongue 46 is moved into the substantially hollow area 40 defined by the second end 38 of the connector 34. The tongue 46 is biased towards the normal position, which is shown in FIG. 3.

Figure 4:
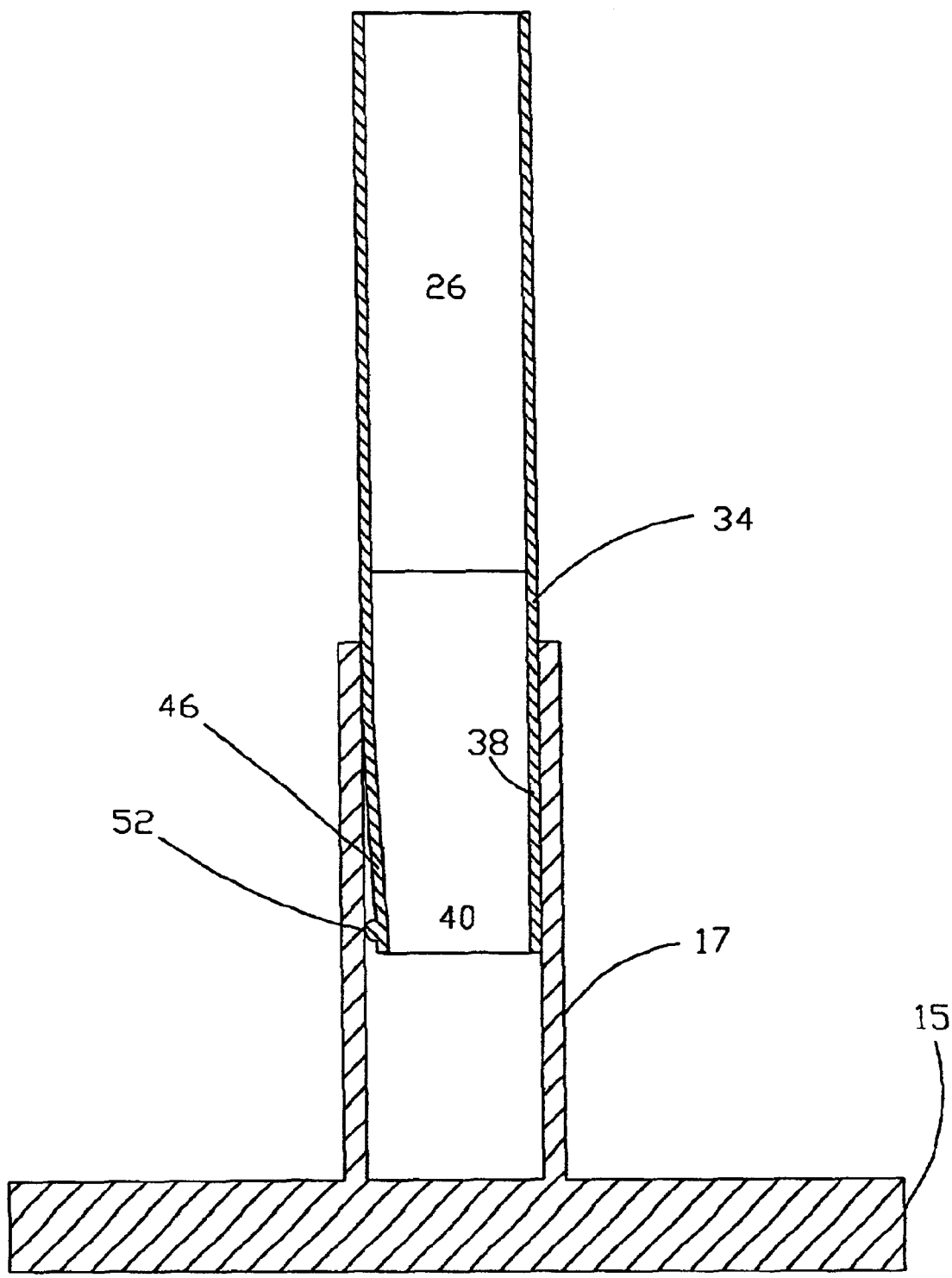
FIG. 4 is a cut away view of the connector when inserted into the first base, showing the tensioned position of the tongue portion of the connector.

FIG. 4 shows the tensioned position of the tongue 46. FIG. 4 also shows the second end 38 of the connector 34 with the hollow space 40 that allows the tongue 46 to be tensionally positioned inside the hollow space 40. As shown in FIG. 4, the connector 34 secures the support assembly 26 to the first base attachment member 17 on the first base 13. Alternatively, the connector 34 can be secured to the second base attachment member 18 on the second base 14 when the connector 34 is inserted into the second base 14. When inserted into the first base attachment member 17 or the second base attachment member 18, the tongue 46 is released from the tension position and allowed to frictionally engage an inside surface of the first base 13 or the second base 14. The connector holds the support assembly 26 and either of the bases 2, 14 together when the raised portion 52 of the tongue 46 frictionally engages the inside surface of one of the bases 2, 14.

While the connector 34 of the appendage elevation system 12 could be comprised of many different types of devices, the connector 34 used in the preferred embodiment is advantageous because it provides enough tension to hold the bases 2, 14 and the support assembly 26 together, even when the first base 13 is moved, while at the same time removing the support assembly 26 from the bases 2, 14 is relatively easy so that a person who is post surgery or has another medical condition can effectively use the elevator system 12 in a home setting.

Figures 5A, 5B, 5C:
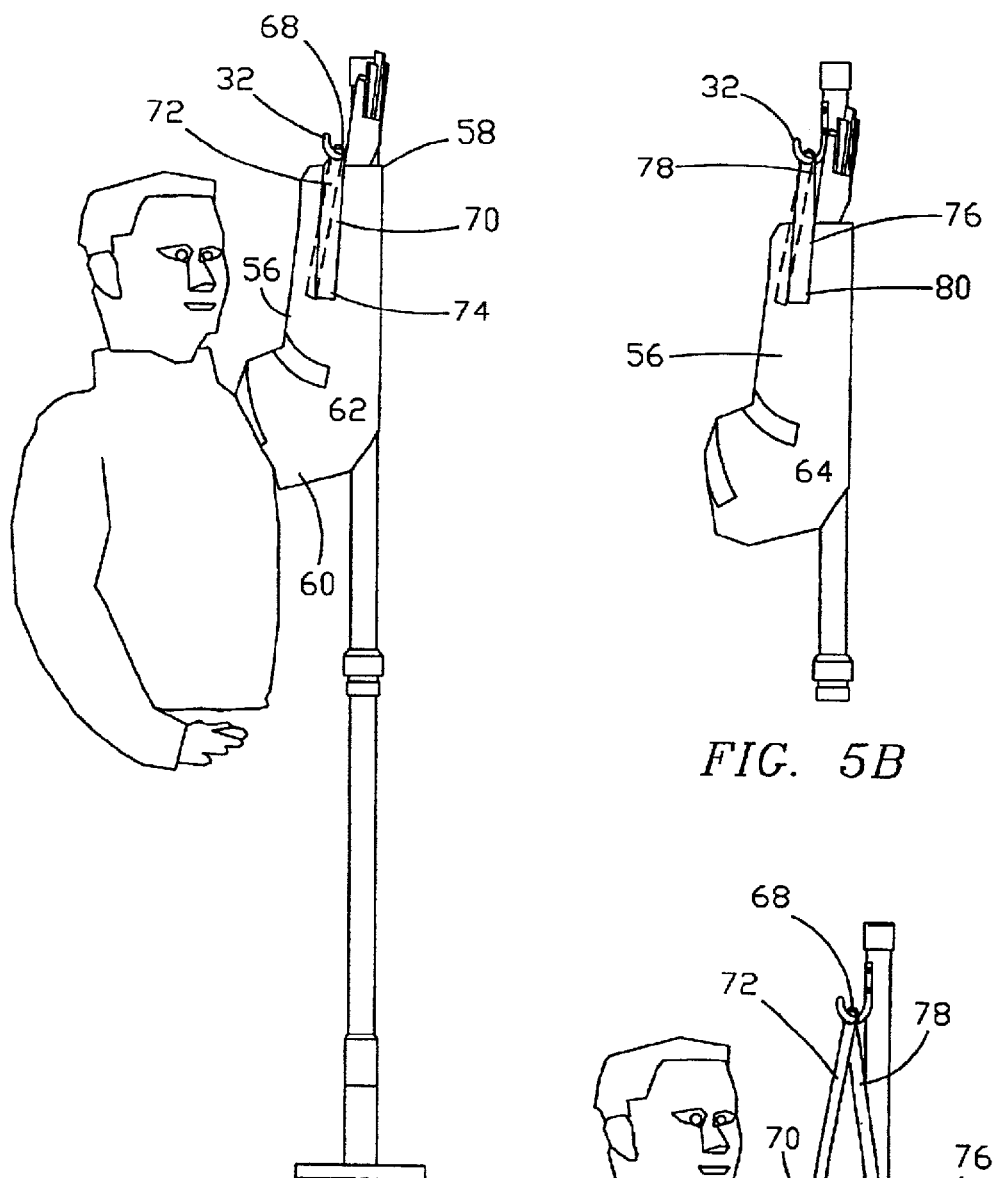
FIGS. 5A, 5B, and 5C are views of the appendage elevator system in use with the first base, showing the varying elevations and positions of the arm in the sling assembly that can be achieved with the system.
Figure 10:
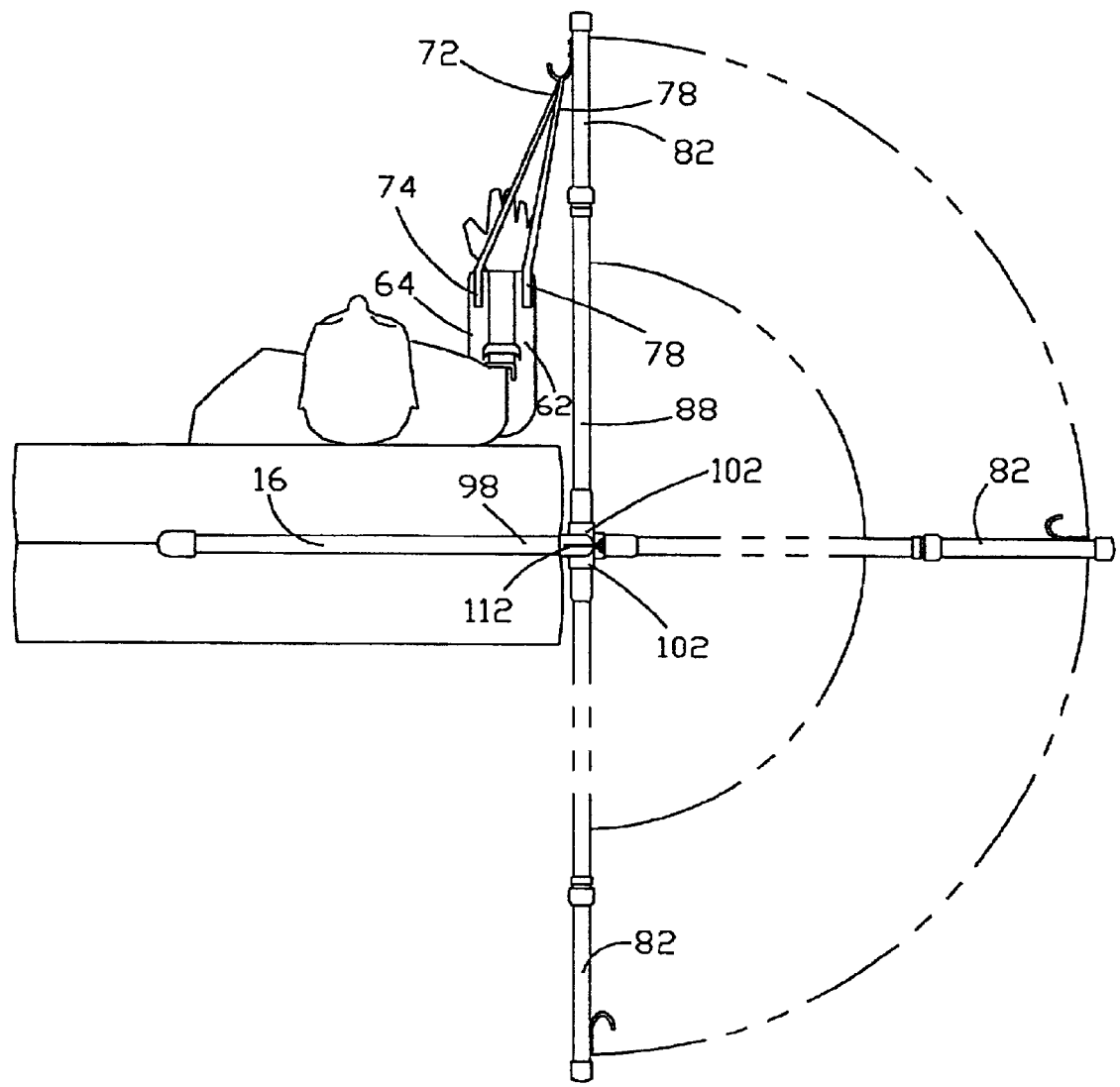
FIG. 10 is a side view of an alternative embodiment of the second base in use, showing the varying positions of the arm elevator that can be achieved relative to the patient and to the supporting surfaces.

The sling assembly 54 of the preferred embodiment, as shown in FIGS. 5A and 5B, is an L-shaped envelope 56 of the usual type which is used to position an arm at a ninety-degree angle at the elbow joint. The L-shaped envelope 56 has a hand end 58 where the hand protrudes from the L-shaped envelope 56 when the arm is inserted into the sling assembly 54 of the preferred embodiment. The L-shaped envelope 56 also has an upper arm end 60, which is located on the L-shaped envelope 56 at the point where the upper arm rests in the L-shaped envelope 56 when the arm is inserted into the sling assembly of the preferred embodiment. Preferably, the sling assembly 54 is used in a manner such that the elbow is bent at a ninety-degree angle with the lower arm in a generally vertical position, and the upper arm in a substantially horizontal position at the upper arm end 60 of the L-shaped envelope 56, with the elbow being in a position that is lower than the hand. Thus, as shown in the FIGS. 5A and 5B, the two straps 70, 76 are positioned at the hand end 58 of the L-shaped envelope 56 near the patient's hand. The sling assembly 54 of the preferred embodiment also has a first outer side 62 and a second outer side 64 which are covered in looped fabric. The two outer sides 62, 64 of the sling assembly 54, as shown in FIGS. 5A, 5B and 10, are preferably covered in "Velcro" material that is adapted to mate with or attach to the fabric engaging hooks on the two straps 70, 76 used to removably attach the sling assembly 54 to the hook 32.

In the preferred embodiment, the means used to removably attach the sling assembly 54 to the hook 32 has three parts as shown in FIGS. 5A, 5B, 5C and 10: (1) a ring 68 or other device adapted to fit onto the hook 32; (2) a first strap 70 of fabric engaging hooks that has a first end 72 attached to the ring 68 and a second end 74 that is attached to the first outer side 62 of the sling assembly 54; and (3) a second strap 76 of fabric engaging hooks that has a first end 78 attached to the ring 68 and a second end 80 that is attached to the second outer side 64 of the sling assembly 54. The two straps 70, 76 are removably attached to the sling assembly 54; the two straps 70, 76 can be attached to the sling assembly 54, removed from the sling assembly 54, and reattached to the sling assembly 54 in a new position by means such as a hook and loop fabric system commonly referred to as "Velcro." The alternative positions are illustrated in FIGS. 5A, 5B, and 5C. The two outer sides 62, 64 of the sling assembly 54 are covered in looped fabric that is adapted to mate or engage with small hooks on the two straps 70, 76, thereby securing the straps to the sling assembly in a manner that is easily adjustable to a variety of positions.

While not a necessary part of the invention, a pillow or other type of cushioning device could be insert into the sling assembly 54 to aid in patient comfort or to position the arm at an angle other than at the ninety-degree angle of the elbow joint when the arm is inserted into the L-shaped envelope 56. In addition, while the preferred embodiment uses a sling adapted for the elevation of an arm, the appendage elevator system 12 could be adapted to accommodate elevation of a leg by substituting a different sling assembly 54 for use with the interchangeable bases 2, 14 of the appendage elevator system 12.

As shown in FIGS. 5A and 5B, the appendage elevator system 12 is vertically adjustable by varying the distance between the hook 32 and the sling assembly 54, which is accomplished by adjusting the two straps 70, 76. An arm can be elevated to a variety of positions depending on where the two straps 70, 76 are placed upon the sling assembly 54. The straps 70, 76 can be placed nearer the upper arm end 60 of the L-shaped envelope 56 of the sling assembly 54 to provide a higher elevation of the arm (shown in FIG. 5A), and the straps 70, 76 can be placed nearer the hand end 58 of the L-shaped envelope 56 of the sling assembly 54 to provide a lower elevation of the arm (shown in FIG. 5B). While the preferred embodiment of the present invention elevates the arm with the hand up and the elbow being positioned below the hand, the appendage elevator system 12 allows for the arm to be elevated in other positions. For example, FIG. 5C shows that the arm can be elevated such that the lower arm and elbow are relatively horizontal and the upper arm is vertical by placing the straps 70, 76 at a different positions on the sling assembly 54.

As shown by FIG. 6, the appendage elevator system 12 can also be adjusted by moving the first support section 82 and the second support section 88 of the support assembly 26 in a linear telescoping manner and securing the two support sections 82, 88 in a desired position using means such as a clamping device 94. FIG. 6 also shows a perspective view of an alternative embodiment of the second base 14 of the present invention. The horizontal frame 16 of the second base 14 has a first end 96 and a second end 98. The first end 96 of the horizontal frame 16 is adapted to be supported by two opposing surfaces such as a mattress and box spring. The alternative embodiment in FIG. 6 also utilizes a pin and aperture system, which is detailed in FIG. 7 and FIG. 8.

Figure 7:
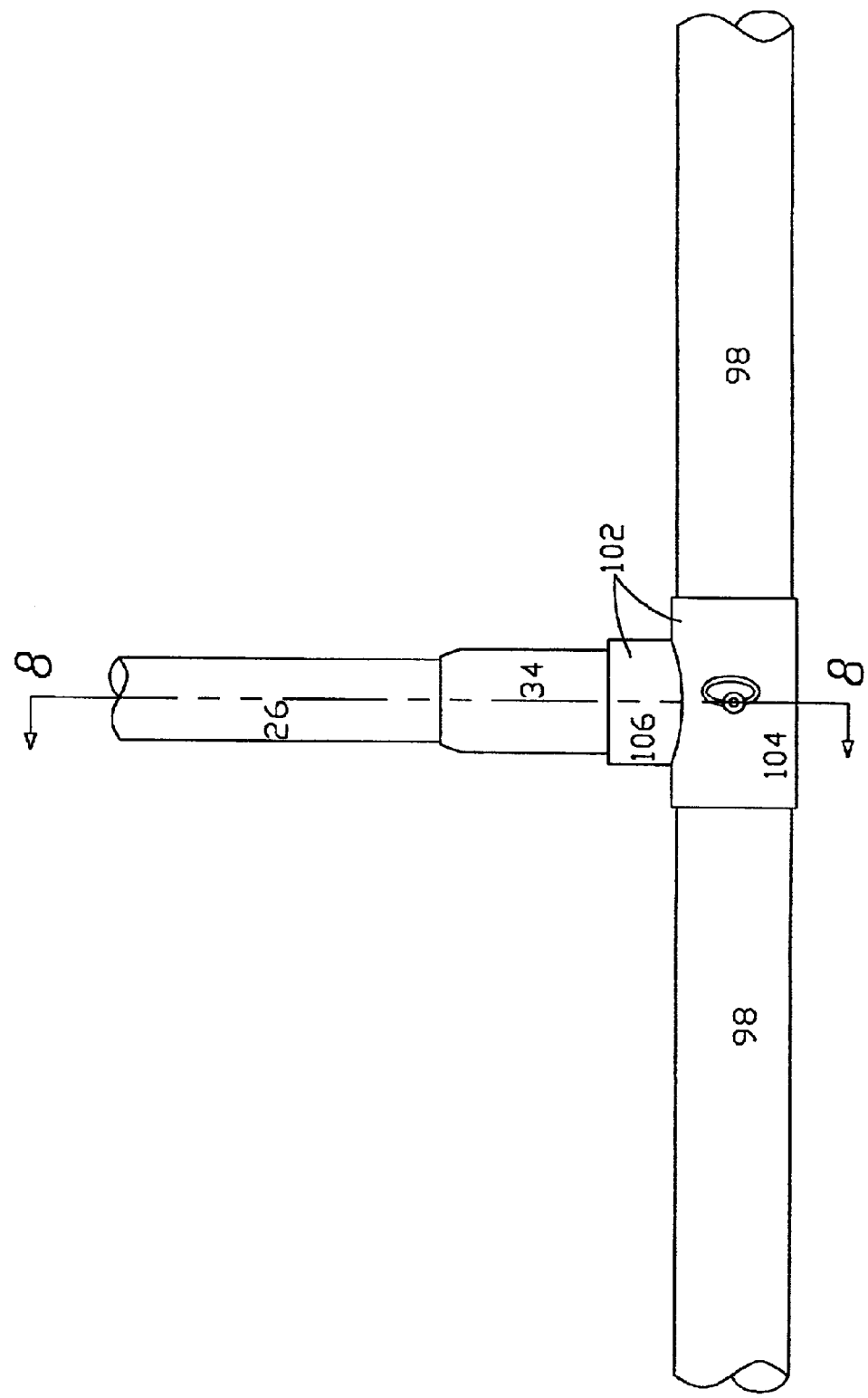
FIG. 7 is an enlarged, detailed view of the horizontal frame shown in FIG. 6 which shows the interconnection of the T-connector and the horizontal frame.

Referring now to FIG. 7, the alternative embodiment of the second base 14 utilizes a T-connector 102 which has a base portion 104 and a perpendicular portion 106 that is attached to the second end 98 of the horizontal frame 16 by inserting a portion of the second end 98 of the horizontal frame 16 into the base portion 104 of the T-connector 102 such that the T-connector 102 is allowed to rotate freely around the second end 98 of the horizontal frame 16. The perpendicular portion 106 of the T-connector 102 defines a hollow space 108 that is adapted to receive the second end 38 of the connector 34 as shown in FIG. 8.

Figure 8:
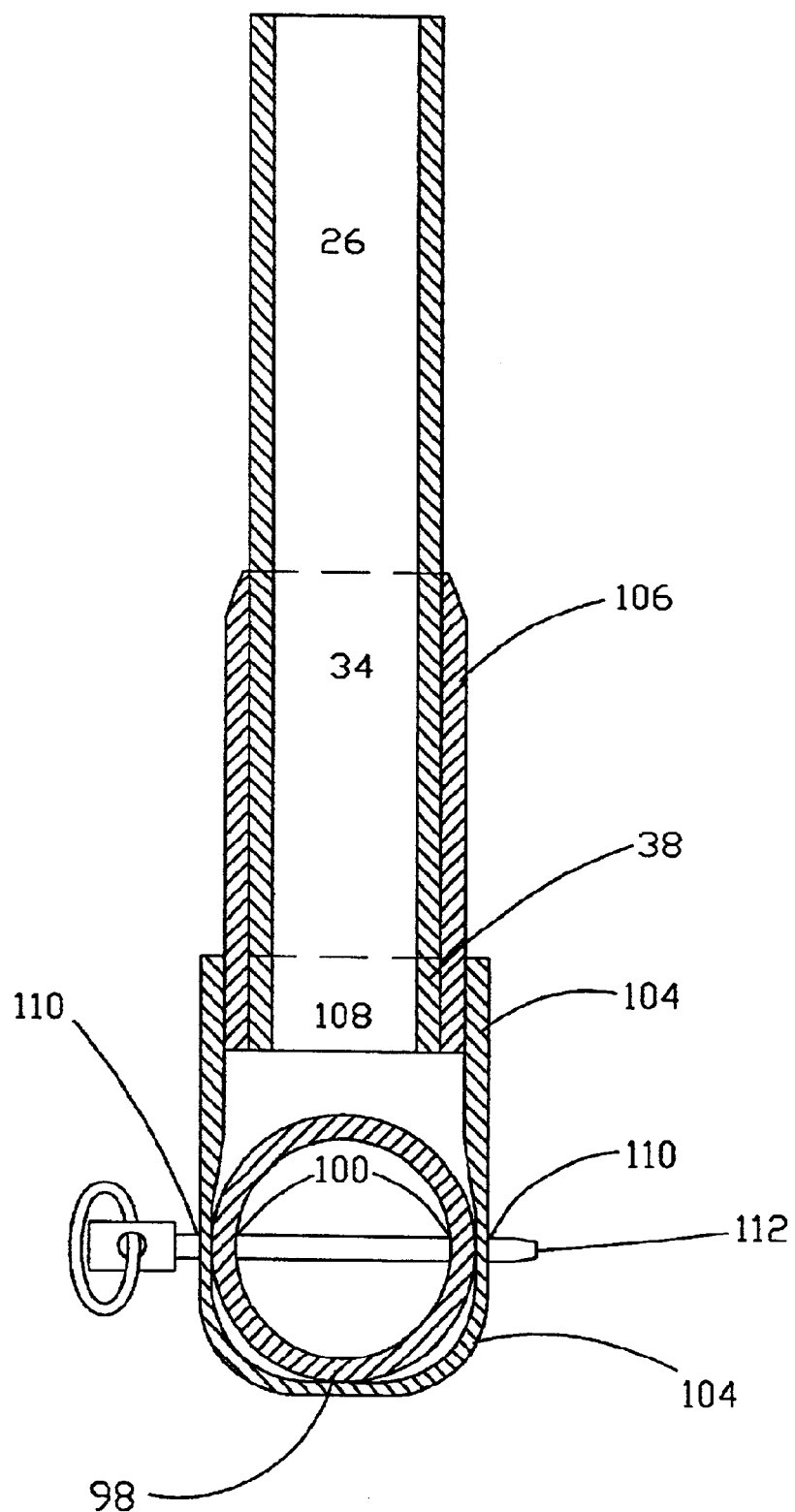
FIG. 8 is a cross section of FIG. 7 along the line 8—8.

FIG. 8 is a cross section of the view shown in FIG. 7 along the line delineated 8—8. FIG. 8 shows that the support assembly 26 is attached to the connector 34 which is inserted into the hollow space 108 defined by the perpendicular portion 106 of the T-connector 102. A first pair of opposing apertures 100 is formed in the second end 98 of the horizontal frame 16. A second pair of opposing apertures 110 is formed in the base portion 104 of the T-connector 102. The second pair of opposing apertures 110 in the base portion 104 of the T-connector 102 can be aligned with the first pair of opposing apertures 100 in the second end 98 of the horizontal frame 16, and a pin 112 which is adapted to pass through the two pairs of opposing apertures 100, 110 can be inserted through the two pairs of opposing apertures 100, 110 to secure the T-connector 102 in a desired position relative to the second end 98 of the horizontal frame 16. FIG. 6 also shows one aperture of the second pair of opposing apertures 110 in the base portion 104 of the T-connector 102, and FIG. 9 shows the pin 112.

Figure 9:
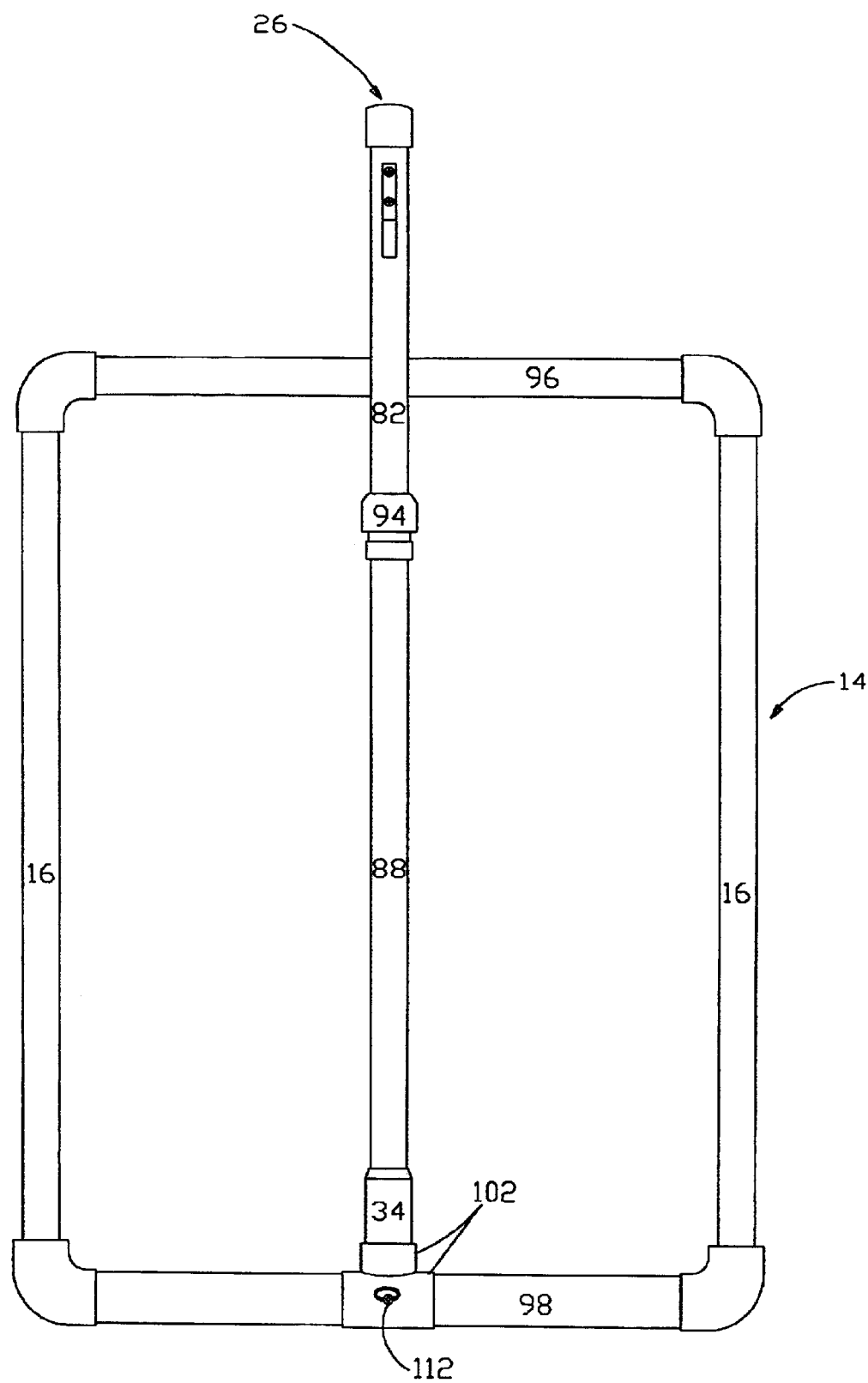
FIG. 9 is a plan view of the alternative embodiment of the second base shown in FIG. 6 in a collapsed position.

FIG. 9 is a plan view that shows how the alternative embodiment of the second base 14 shown in FIG. 6 can be collapsed for storage or transport. The second base 14 can be collapsed by removing the pin 112 and rotating the T-connector 102 towards the first end 96 of the horizontal frame 16 thereby moving the support assembly 26 to a relatively coplanar position with the horizontal frame 16, and making the second base 14 relatively flat for storage and transport. Furthermore, if desired, the connector 34 can be removed from the T-connector 102, separating the support assembly 26 from the second base 14. Finally, if desired, the first support section 82 can be disengaged from the second support section 88 by removing the clamping device 94, reducing the appendage elevator system 12 to small, lightweight parts that are easy to store and transport.

FIG. 10 shows how the T-connector 102 can be rotated while the appendage elevator system 12 with the alternative embodiment of the second base 14 is in use. The free rotation of the T-connector 102 about the second end 98 of the horizontal frame 16 allows a nurse or other caretaker to access a patient without removing the second base 14 from between the opposing surfaces. To access the patient, the pin 112 is removed, and the T-connector 102 is then rotated about the second end 98 of the horizontal frame 16. Adjustable positioning of the support assembly is useful in that it allows easier access to the patient and would allow more freedom of movement for a patient entering and exiting the bed. The downward position shown in FIG. 10 can also be used for storage of appendage elevator system 12 utilizing this alternative embodiment of the second base 14.

Many modifications and variations of the present invention are possible in light of the above teachings. For example, other materials can be substituted for the lightweight plastic tubing or PVC pipe, such as lightweight aluminum. The means for securing the sling assembly 54 to the hook 32 or the means for securing the telescoping support sections 82, 88 could also be varied without materially altering the invention. In addition, a different connector 34 could be used to attach the support assembly 26 to the first base 13 or second base 14, such as a clamp or a threaded design on the pieces so that they twist together. Also, the pin and aperture system could be replaced with a push-button release mechanism. Therefore, within the scope of the appended claims, the present invention may be practiced otherwise than as specifically described. Thus, the present invention has been described in an illustrative manner. It is to be understood that the terminology that has been used is intended to be in the nature of words of description, rather than of limitation. It will be understood by those skilled in the art that various changes and modifications can be made without departing from the scope of the invention as defined in the claims.

What is claimed is:

1. A system for appendage elevation comprising:
    a first base adapted to rest on a flat surface;
    a first base attachment member having a first end and a second end, said first end of said first base attachment member being operably attached to and extending from said first base such that said first base attachment member is supported by said first base, said second end of said first base attachment member defining a hollow space;

a generally planar horizontal frame adapted to be supported between opposing surfaces;

a second base attachment member having a first end and a second end, said first end of said second base attachment member being operably attached to and extending from said horizontal frame such that said horizontal frame supports said second base attachment member, said second end of said second base attachment member defining a hollow space;

a support assembly having a first end and a second end;

a hook, operably attached near said first end of said support assembly;

a connector having a first end and a second end, said first end of said connector being operably attached to said second end of said support assembly, said second end of said connector being removably insertable into said first base or said second base, and said second end of said connector defining a hollow space;

a first groove originating at said second end of said connector and extending into said connector in a longitudinal fashion relative to said support assembly;

a second groove originating at said second end of said connector and extending into said connector, substantially parallel to said first groove and in a longitudinal fashion relative to said support assembly;

a tongue formed between said first groove and said second groove, said tongue having a first end and a second end, said first end of said tongue being attached to said second end of said connector, said second end of said tongue being moveable between a normal position wherein said tongue is substantially aligned with said second end of said connector and a tensioned position wherein said tongue is moved into said substantially hollow area of said second end of said connector, said tongue being biased towards said normal position, and said tongue being adapted to frictionally engage an inside surface of said first base or an inside surface of said second base;

wherein said tongue further comprises a raised portion near said second end of said tongue, said raised portion being adapted to frictionally engage said inside surface of said first base or said inside surface of said second base when said tongue is released from said tensioned position thereby allowing said raised portion of said tongue to contact said inside surface of said first base or said inside surface of said second base when said connector is inserted into said first base or said second base;

a sling assembly having a first outer side covered in looped fabric and a second outer side covered in looped fabric;

a ring adapted to be placed on said hook;

a first strap of fabric-engaging hooks having a first end and a second end, said first end of said first strap being attached to said ring and said second end of said first strap being removably attached to the first outer side of said sling assembly; and a second strap of fabric-engaging hooks and having a first end and a second end, said first end of said second strap being attached to said ring and said second end of said second strap being removably attached to the second outer side of said sling assembly.

2. A system for appendage elevation comprising:

a first base adapted to rest on a flat surface;

a first base attachment member having a first end and a second end, said first end of said first base attachment member being operably attached to and extending from said first base such that said first base attachment member is supported by said first base, said second end of said first base attachment member defining a hollow space;

a horizontal frame having a first end and a second end, said first end of said horizontal frame being adapted to be supported between opposing surfaces, and said second end of said horizontal frame defining a first pair of opposing apertures;

a T-connector having a base portion and a perpendicular portion, said base portion of said T-connector being adapted to allow insertion of said second end of said horizontal frame such that said T-connector rotates freely about said horizontal frame, and said base portion of said T-connector defining a second pair of opposing apertures adapted such that said second pair of opposing apertures can be aligned with said first pair of opposing apertures in said horizontal frame, said perpendicular portion of said T-connector defining a hollow space to receive said second end of said connector; and a pin adapted to slide into and pass through said first pair of opposing apertures in said horizontal frame and said second pair of opposing apertures in said base portion of said T-connector to secure said T-connector in a desired position relative to said horizontal frame;

a support assembly having a first end and a second end;

a hook, operably attached near said first end of said support assembly;

a connector having a first end and a second end, said first end operably attached to said second end of said support assembly, and said second end being removably insertable into said first base or said second base;

a sling assembly having a first outer side covered in looped fabric and a second outer side covered in looped fabric;

a ring adapted to be placed on said hook; a first strap of fabric-engaging hooks having a first end and a second end, said first end of said first strap being attached to said ring and said second end of said first strap being removably attached to the first outer side of said sling assembly; and a second strap of fabric-engaging hooks and having a first end and a second end, said first end of said second strap being attached to said ring and said second end of said second strap being removably attached to the second outer side of said sling assembly.

3. The system according to claim 2 wherein said support assembly comprises:

a first support section having a first end and a second end;

a second support section having a first end and a second end, said first end of said second support section being telescopically insertable into said second end of said first support section; and a means to selectively secure said first end of said second support section in a telescopic fashion relative to said second end of said first support section.

4. The system according to claim 3 wherein said means to selectively secure said first end of said second support section in a telescopic fashion relative to said second end of said first support section is a clamping device.

5. The system according to claim 2 wherein said second end of said connector comprises:

a first groove originating at said second end of said connector and extending into said connector in a longitudinal fashion relative to said support assembly; and a second groove originating at said second end of said connector and extending into said connector, substantially parallel o said first groove and in a longitudinal fashion relative to said support assembly.

6. The system according to claim 5 wherein said first groove and said second groove define a tongue having a first end and a second end, said first end of said tongue being attached to said second end of said connector, said second end of said tongue being moveable between a normal position wherein said tongue is substantially aligned with said second end of said connector and a tensioned position wherein said tongue is moved into said substantially hollow area of said second end of said connector, said tongue being biased towards said normal position, and said tongue being adapted to frictionally engage an inside surface of said first base or an inside surface of said second base.

7. The system according to claim 6 wherein said tongue further comprises a raised portion near said second end of said tongue, said raised portion being adapted to frictionally engage said inside surface of said first base or said inside surface of said second base when said tongue is released from said tensioned position thereby allowing said raised portion of said tongue to contact said inside surface of said fist base or said inside surface of said second base when said connector is inserted into said first base or said second base.

8. A system for appendage elevation comprising:

a first base comprising a weighted portion adapted to rest on a flat surface and a first base attachment member having a first end and a second end, said first end of said first base attachment member being operably attached to and extending from said weighted portion such that said first base attachment member is supported by said weighted portion, and said second end of said first base attachment member defining a hollow space to receive a second end of a connector;

a second base adapted to be supported between opposing surfaces, said second base comprising a horizontal frame having a first end and a second end, said first end of said horizontal frame being adapted to be supported between two opposing surfaces, and said second end of said horizontal frame defining a first pair of opposing apertures; a T-connector having a base portion and a perpendicular portion, said base portion of said T-connector being adapted to allow insertion of said second end of said horizontal frame such that said T-connector rotates freely about said horizontal frame, and said base portion of said T-connector defining a second pair of opposing apertures adapted such that said second pair of opposing apertures can be aligned with said first pair of opposing apertures in said horizontal frame, said perpendicular portion of said T-connector defining a hollow space to receive said second end of said connector; and a pin adapted to slide into and pass through said first pair of opposing apertures in said horizontal frame and said second pair of opposing apertures in said base portion of said T-connector to secure said T-connector in a desired position relative to said horizontal frame;

a support assembly having a first end and a second end;

a hook, operably attached near said first end of said support assembly;

said connector further comprising a first end in addition to said second end, said first end of said connector being operably attached to said second end of said support assembly, and said second end of said connector being removably insertable into said first base and said second base;

a sling assembly; and a means for removably attaching said sling assembly to said hook.

9. A system for appendage elevation comprising:

a first base;

a second base adapted to be supported between opposing surfaces, said second base comprising a horizontal frame having a first end and a second end, said first end of said horizontal frame being adapted to be supported between two opposing surfaces, and said second end of said horizontal frame defining a first pair of opposing apertures; a T-connector having a base portion and a perpendicular portion, said base portion of said T-connector being adapted to allow insertion of said second end of said horizontal frame such that said T-connector rotates freely about said horizontal frame, and said base portion of said T-connector defining a second pair of opposing apertures adapted such that said second pair of opposing apertures can be aligned with said first pair of opposing apertures in said horizontal frame, said perpendicular portion of said T-connector defining a hollow space to receive a second end of a connector; and a pin adapted to slide into and pass through said first pair of opposing apertures in said horizontal frame and said second pair of opposing apertures in said base portion of said T-connector to secure said T-connector in a desired position relative to said horizontal frame a support assembly having a first end and a second end;

a hook, operably attached near said first end of said support assembly;

said connector further comprising a first end in addition to said second end, said first end of said connector being operably attached to said second end of said support assembly, and said second end of said connector being removably insertable into said first base and said second base;

a sling assembly; and a means for removably attaching said sling assembly to said hook.

10. A system for appendage elevation comprising:

a first base;

a second base adapted to be supported between opposing surfaces;

a support assembly having a first end and a second end;

a hook, operably attached near said first end of said support assembly;

a connector having a first end and a second end, said first end of said connector being operably attached to said second end of said support assembly, and said second end of said connector being removably insertable into said first base and said second base, wherein said second end of said connector defines a substantially hollow area and said second end of said connector comprises a first groove originating at said second end of said connector and extending into said connector in a longitudinal fashion relative to said support assembly, and a second groove originating at said second end of said connector and extending into said connector, substantially parallel to said first groove and in a longitudinal fashion relative to said support assembly;

wherein said first groove and said second groove define a tongue having a first end and a second end, said first end of said tongue being attached to said second end of said connector, said second end of said tongue being moveable between a normal position wherein said tongue is substantially aligned with said second end of said connector and a tensioned position wherein said tongue is moved into said substantially hollow area of said second end of said connector, said tongue being biased towards said normal position, and said tongue being adapted to frictionally engage an inside surface of said first base or an inside surface of said second base;

wherein said tongue further comprises a raised portion near said second end of said tongue, said raised portion being adapted to frictionally engage said inside surface of said first base or said inside surface of said second base when said tongue is released from said tensioned position thereby allowing said raised portion of said tongue to contact said inside surface of said first base or said inside surface of said second base when said connector is inserted into said first base or said second base;

a sling assembly; and a means for removably attaching said sling assembly to said hook.

* * * * *